(12) United States Patent
McDonald

(10) Patent No.: US 9,883,922 B2
(45) Date of Patent: Feb. 6, 2018

(54) DENTAL WEDGE

(71) Applicant: Simon Paul McDonald, Katikati (NZ)

(72) Inventor: Simon Paul McDonald, Katikati (NZ)

(73) Assignee: Dentsply Sirona Inc., York, PA (US)

( * ) Notice: Subject to any disclaimer, the term of this patent is extended or adjusted under 35 U.S.C. 154(b) by 130 days.

(21) Appl. No.: 14/556,092

(22) Filed: Nov. 28, 2014

(65) Prior Publication Data

US 2015/0150651 A1 Jun. 4, 2015

(30) Foreign Application Priority Data

Nov. 29, 2013 (NZ) .......................... 618394

(51) Int. Cl.
| | | |
|---|---|---|
| A61C 7/00 | (2006.01) | |
| A61C 5/12 | (2006.01) | |
| A61C 5/85 | (2017.01) | |
| A61C 5/88 | (2017.01) | |

(52) U.S. Cl.
CPC ................ *A61C 5/127* (2013.01); *A61C 5/85* (2017.02); *A61C 5/88* (2017.02); *A61C 2201/007* (2013.01)

(58) Field of Classification Search
CPC ... A61C 5/127; A61C 5/125; A61C 2201/007; A61C 5/85; A61C 5/88
USPC ................................ 433/149, 148, 153, 162
See application file for complete search history.

(56) References Cited

U.S. PATENT DOCUMENTS 6,988,887 B2 * 1/2006 Hansen ..................... A61C 7/00
433/148

7,083,412 B1 * 8/2006 Karapetyan .............. A61C 5/85
433/148
2007/0054233 A1 3/2007 Rizoiu
2008/0058907 A1 3/2008 Reuben
2015/0004556 A1 1/2015 Jin

FOREIGN PATENT DOCUMENTS

WO 2005/064993 A1 7/2005

OTHER PUBLICATIONS

Matthey, Johnson. "How Does Nitinol Work? Nitinol Shape Memory and Superelasticity." Mar. 25, 2012 capture from the Wayback Machine, https://web.archive.org/web/20120325211520/ http://jmmedical.com/resources/122/How-Does-Nitinol-Work%3F-Al 1-About-Nitinol-Shape-Memory-and-Superelasticity.html.*

* cited by examiner

*Primary Examiner* — Michael Carey
(74) *Attorney, Agent, or Firm* — Leana Levin; Douglas J. Hura; David A. Zdurne

(57) ABSTRACT

A dental wedge for inserting into the interproximal space between adjacent teeth comprises a first and second sidewall comprised of a shape memory material, including a nickel-titanium alloy, wherein the dental wedge is in a first, resting state when outside of the interproximal space and transforms to a second, operational state when the dental wedge is interested into the interproximal space between adjacent teeth and exposed to a first transformation stimulus, namely exposure to the higher temperature in the interproximal space. The expansion force generated by the dental wedge when in the second, operational stage is sufficient to secure a dental matrix against the tooth being restored and to separate the tooth being restored and adjacent tooth to expand the interproximal space.

24 Claims, 7 Drawing Sheets

DENTAL WEDGE

CROSS-REFERENCE TO RELATED APPLICATIONS

This application claims the benefit of New Zealand Provisional Specification Serial No. 618394, filed Nov. 29, 2013, the contents of which are incorporated by reference herein.

FIELD OF THE INVENTION

The present invention relates to dental wedges for use during direct restoration of teeth having damaged portion or dental carries requiring restoration.

BACKGROUND OF THE INVENTION

Direct dental restorations typically involves the use of devices to separate the tooth being restored from the adjacent tooth to increase the interproximal space between the teeth and to secure a dental matrix against the tooth being restored to prevent undesirable flow of the dental restoration material from the restoration area. The mechanical expansion force required to accomplish these tasks is typically provided by a matrix retainer clip and supplemented by a dental wedge to secure the matrix to the tooth at the gingival margin. However, the interproximal space between the teeth is small and may not have uniform, convenient dimensions rendering the use of multiple devices in a crowded space more cumbersome that necessary for dental professionals to quickly and accurately restore teeth.

SUMMARY OF THE INVENTION

The present invention is a dental wedge with the benefit of enabling a dentist to more easily separate adjacent teeth during a restorative procedure and support a dental matrix band for the same purpose. The dental inserts into the interproximal space between a first tooth being restored and a second, adjacent tooth and comprises a first sidewall comprising an internal portion and configured to engage the first tooth; a second sidewall comprising an internal portion and configured to engage the second tooth; and a bridge disposed between and connecting the first sidewall and second sidewall to form an inverted V-shaped cross section throughout the internal portions of the first sidewall and second sidewall. The first sidewall and second sidewall consisting essentially of a shape memory material enabling the first sidewall and second sidewall to transform from a first, resting state wherein the dental wedge is readily deformable to a second, operational state wherein the dental wedge returns to a preformed shape and exerts an expansion force on the first tooth being restored and the second, adjacent tooth. The shape memory material comprises a shape memory alloy, and is preferably a nickel-titanium alloy. The shape memory material can also be a shape memory polymer.

DETAILED DESCRIPTION OF THE DRAWINGS

Figure 1:
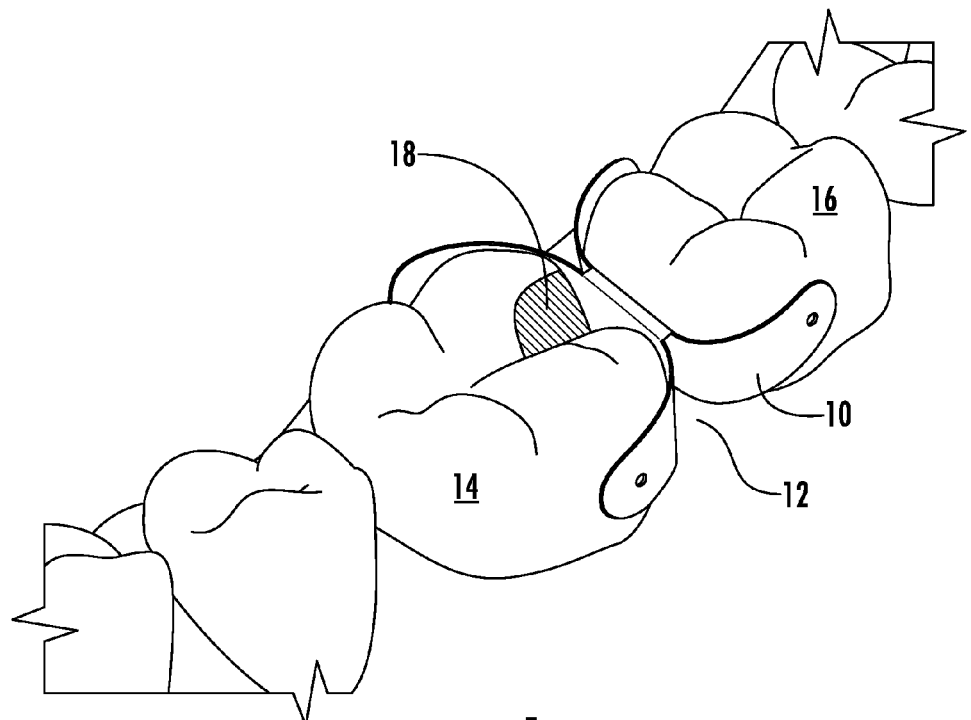
FIGS. 1 and 2 are perspective views of an embodiment of the present invention.
Figure 2:
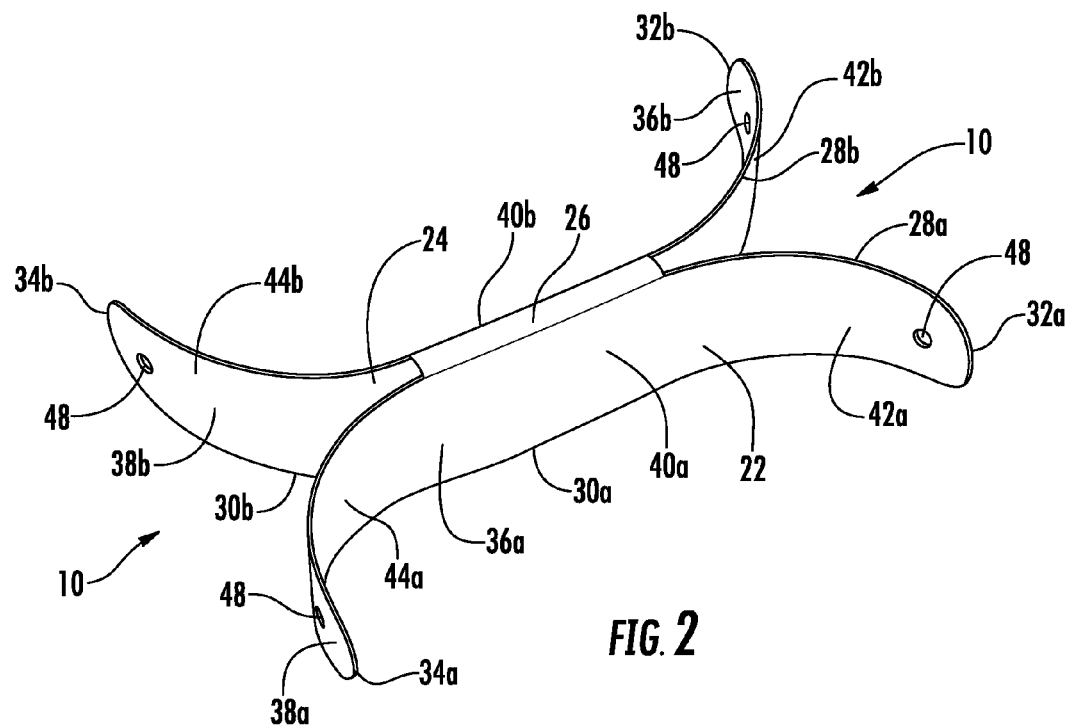
Figure 3:
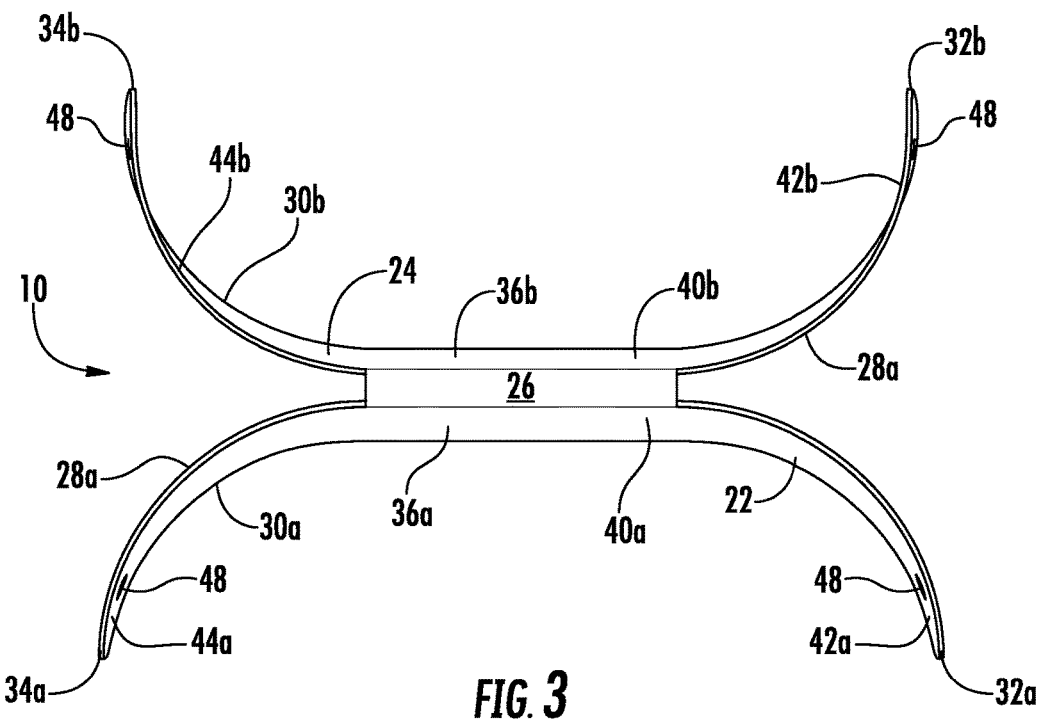
FIG. 3 is a top plan view of an embodiment of the present invention.
Figure 4:
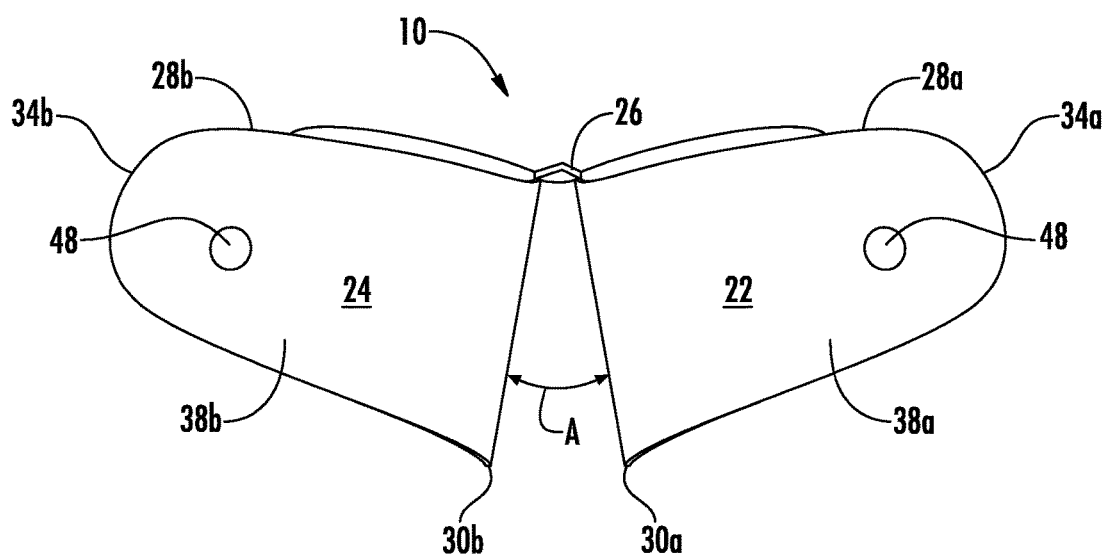
FIG. 4 is a side elevation and perspective view of an embodiment of the present invention.
Figure 5:
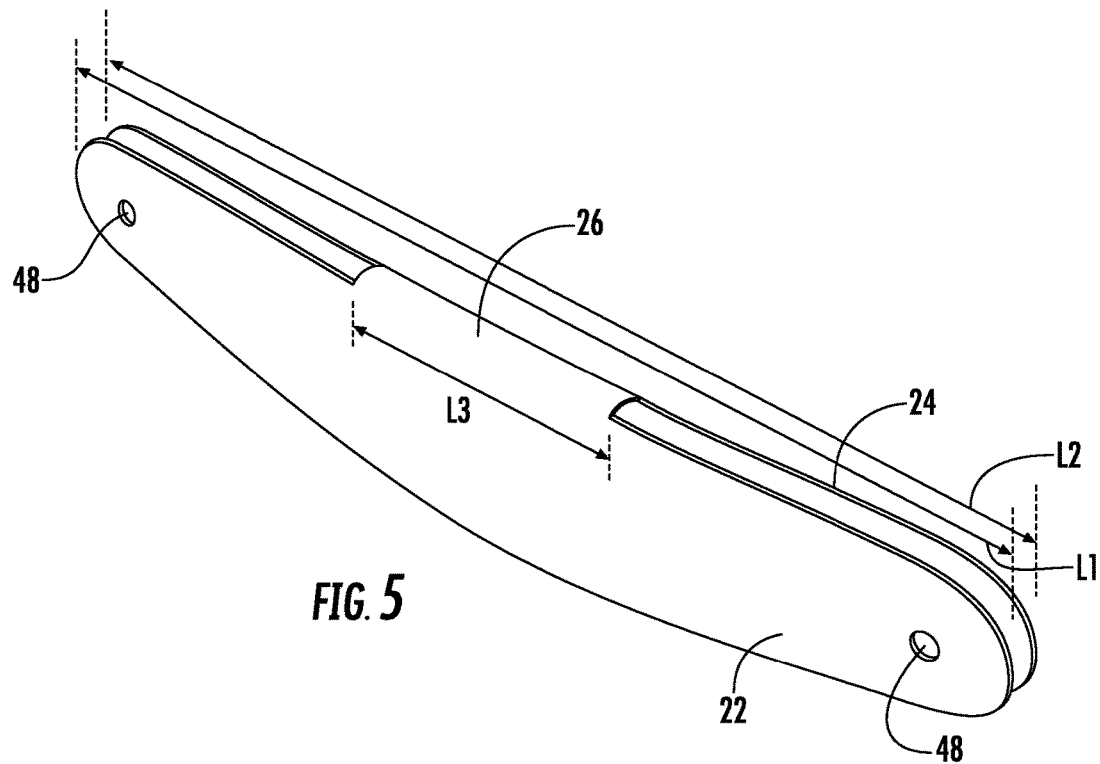
FIG. 5 is a perspective view of an embodiment of the present invention.
Figure 6:
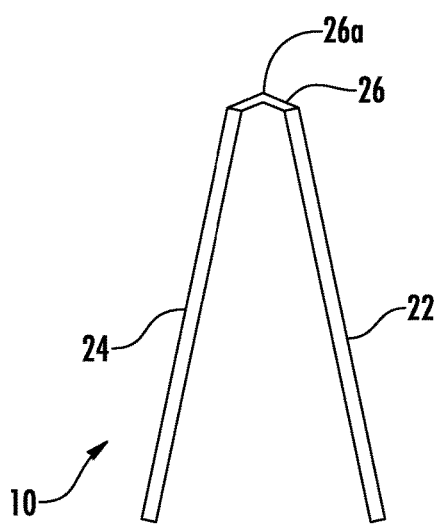
FIGS. 6 and 7 are side elevation views of embodiments of the present invention.
Figure 7:
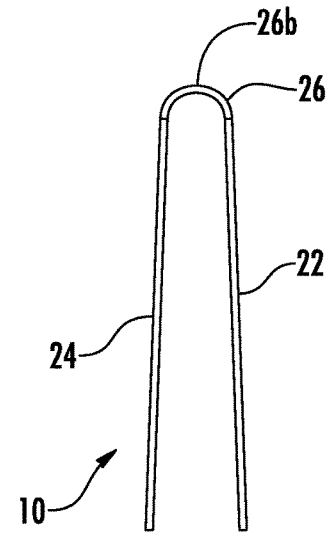
Figure 8:
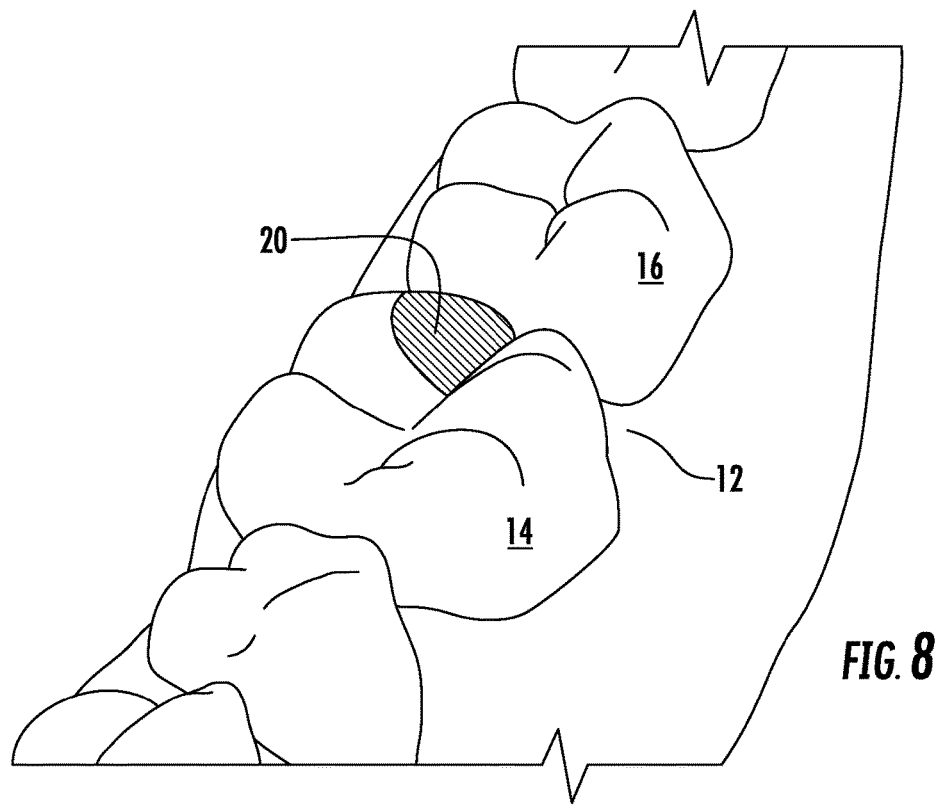
FIGS. 8-15 are perspective views of dental wedges in accordance with the present invention.

FIGS. 1-15 show various views of a dental wedge 10 in accordance with the present invention for use in direct dental restoration procedures. FIG. 1 shows a dental wedge 10 placed in the interproximal space 12 between a first tooth being restored 14 and a second adjacent tooth 16. In this figure the restoration area 18 is prepared to receive the restoration material after removal of the dental carry or damaged area 20 (FIG. 8) of the tooth being restored 14 by standard dental procedures and protocols. Turning to FIGS. 2-4, the dental wedge 10 comprises a first and second sidewall 22, 24 and a bridge 26 disposed between and connecting the first and second sidewall 22, 24. When straightened (FIG. 5), the first and second sidewalls 22, 24 each have a length L1, L2 and in the present embodiment the length L3 of the bridge 26 is less than the length L1, L2 of the first and second sidewalls 22, 24. The length L3, as shown, is approximately ⅓ to ½ of the length L1, L2 of the first and second sidewalls 22, 24. The bridge 26 is generally planar, but may have a have a ridge 26a with surfaces diverging therefrom or a radiused curve 26b (FIG. 6, FIG. 7) to ease manufacture of the dental wedge 10.

Each of the first and second sidewalls 22, 24 comprises a top edge 28a, b, bottom edge 30a, b, and opposing side edges 32a, b, 34a, b, and interior 36a, b and exterior 38a, b surfaces. The top edges 28a, b shown in FIGS. 2-3 are simple, generally one-dimensional curves, but can be adapted to comprise complex, multi-dimensional curvature or other contour as may be required for a particular application or placement of the dental wedge 10. The bottom edges 30a, b are shown to be a gently downward radiused curve, but can also be formed as a straight edge or with a greater radiused curve as may be required for a particular application or placement of the dental wedge 10. The bottom edges 30a, b may also curve away from each other with a similar curvature to the top edge 28a, b. The opposing side edges 32a, b and 34a, b are curved to ease insertion of the dental wedge 10 into the interproximal space 12 between the tooth being restored 14 and the adjacent tooth 16.

Figure 9:
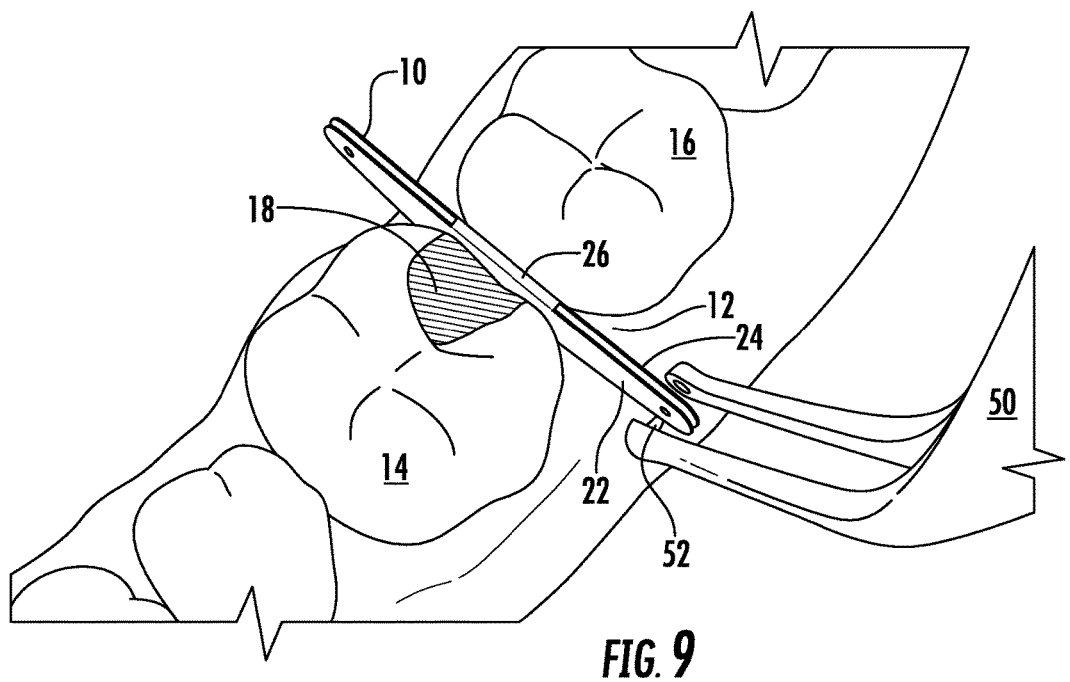
Figure 10:
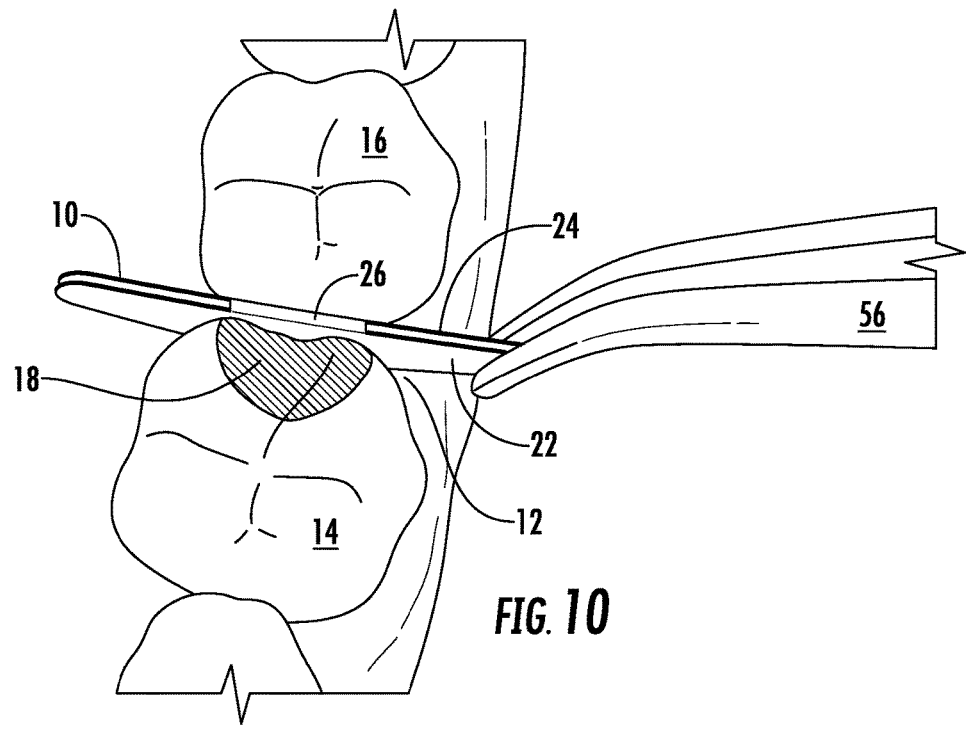

The first and second sidewalls 22, 24 further comprises an interior portion 40a, b and first and second wings 42a, b, 44a, b extending from opposing sides of the interior portions 40a, b of the first and second sidewalls 22, 24. As seen in FIG. 3, the length L4 of the interior portions 42a, b corresponds to the length of the bridge 26 with the balance of the lengths L1, L2 of the first and second sidewalls 22, 24 apportioned to the wings 42a, b, 44a, b. The wings 42a, b, 44a, b of the sidewalls 22, 24 may be curve and configured to wrap around the tooth being restored 14 and the adjacent tooth 16 to assist in securing the dental matrix 46 (FIG. 15) in position. In another embodiment of the invention the wings 42a, b, 44a, b not curve and remain coplanar with the interior portions 40a, b. Each of the wings 42a, b, 44a, b may include a through-hole 48 configured to receive the pin portion 52 of a pin-tweezers 50 to enable the user of the dental wedge 10 to grab and manipulate the placement of the dental wedge 10 within the interproximal space 12 (FIG. 9). In the absence of through-holes, the user of the dental wedge 10 can use another suitable dental instrument 56, such as a tweezers, forceps, or other suitable instrument to grab the sidewalls 22, 24 of the dental wedge 10 (FIG. 10). As shown in FIG. 4, the general cross-sectional configuration of the dental wedge 10, at least throughout the interior portions 40a, b of the sidewalls 22, 24 is of an inverted V-shape, wherein the sidewalls 22, 24 converge towards each other as each sidewalls extends from its bottom edge 30a, b to its top edge 28a, b.

The first and second sidewalls 22, 24 and bridge 26 of the dental wedge 10 are comprised of a shape memory material that enables the dental wedge 10 to transform from a first, resting state to a second, operational state in the presence of and in response to a first transformation stimulus. The use of the shape memory material also enables the dental wedge 10 to transform from the second state back to the first stage when the first transformation stimulus is removed or in the presence of a second transformation stimulus. The shape memory material may be a shape memory alloy or shape memory polymer that are biocompatible and exhibit suitable shape memory and superelastic properties. The dental wedge 10 manufactured from such a shape memory material will be inserted into the interproximal space between the tooth being restored and adjacent tooth when the dental wedge is in its first, resting state and will transform the second, operational state in response to a first transformation stimulus, namely, the increased temperature in the patient's mouth. The transformation activates a compressive force that is sufficient to both separate the adjacent teeth and secure a dental matrix against the tooth being restored. The expansion force is continuously applied as long as the dental matrix remains in the second state. Removing the dental wedge 10 from the patient's mouth, thereby removing the first transformation stimulus, enables the dental wedge to 10 return to its first, resting state. Exposing the dental wedge 10 to a second transformation stimulus, such as the cool environment of a refrigerator or a coolant spray also enables the dental wedge 10 to return to the first, resting state.

Shape memory alloys suitable for the making the dental wedge 10 of the present invention include alloys composed substantially of nickel and titanium (NiTi) or alloys of other metals known to exhibit shape memory effects, such as CuZnAl, CuAlNi, FeNiAl, and InTi. Elements such as boron, cerium, cobalt, iron, copper, vanadium, and zirconium may also be added to tailor the mechanical properties to the intended application. One exemplary shape memory alloy is nitinol (NiTi). NiTi undergoes a phase transformation in its crystal structure when heated from its weaker, low temperature phase (Martensite) to its stronger, high temperature phase (Austenite) and from Austentite to Martensite during a cooling process. In the Martensitic phase, the NiTi is readily workable and malleable and the dental wedge 10 may be manipulated into a configuration rendering it easier for the dental professional to insert the wedge 10 into the interproximal space between the tooth being restored and the adjacent tooth. As shown in FIG. 3, the dental wedge 10 has a generally inverted V-shaped cross section and when the NiTi of the dental wedge 10 is in its Martensite phase the bottom edges of the sidewalls may be readily pinched together or otherwise manipulated to reduce the overall footprint of the dental wedge 10. Once the dental wedge 10 is inserted into the interproximal space the higher temperature encountered in the patient's mouth, the first transformation stimulus, the NiTi will transform to its Austenite phase and the dental wedge 10 will return to its original shape. When NiTi is heated through its transformation temperatures, (its Austenite start temperature $A_S$ and Austenite finish temperature $A_F$) it reverts to its Austenite structure and forcefully recovers its previous shape, e.g. the dental wedge shown in FIG. 1.

Useful shape memory polymers include segmented linear polyurethanes having hard segments and a soft segments. The hard segments are typically crystalline, with a defined melting point, and the soft segments are typically amorphous, with a defined glass transition temperature. Suitable polymers used to prepare the hard and soft segments include various polyethers, polyacrylates, polyamides, polysiloxanes, polyurethanes, polyether amides, polyurethane/ureas, polyether esters, urethane/butadiene copolymers, and polyesters. Examples of shape memory polymers are described in U.S. Pat. No. 6,169,084 to Langer et al., U.S. Pat. No. 5,145,935 to Hayashi et al., U.S. Pat. No. 5,665,822 to Bitler et al., and U.S. Pat. No. 5,506,300 to Ward et al.

The dental wedge 10 of the present invention made from a shape memory alloy, such as NiTi metal alloy, is shaped into the form seen in appended figures by a series of steps involving bending, twisting, or squeezing of a sheet of the raw material, and made to retain its new shape using a combination of mechanical and thermal "training" or "setting" steps. The training/setting process generally involves heating the formed configuration to a suitable heat treatment temperature and quickly cooling it in a water bath or by rapid air cooling, thus freezing the NiTi's crystalline structure in a new position.

The dental wedge 10 may be formed from a sheet of NiTi material with a thickness of approximately 0.1-0.5 mm. The basic, two-dimensional shape of the wedge can be stamped, cut, laser or chemical etched from the sheet of raw material and then shaped into its desired form. The height of the sidewalls 22, 24 is approximately 3-4mm and the angle A of the sidewalls is approximately 30 deg. The width of the bridge 26 may vary for use in interproximal spaces of different dimension. If the interproximal space is wide it will be desirable to have a wider bridge 26 to avoid a requirement for taller sidewalls 22, 24. The overall length of each sidewall 42, 44 is selected based on the intended application of the dental wedge 10 and the length of the bridge 26, and corresponding length of the wings 42a, b and 44a, b is selected also based on the desired wrap around on the first and second teeth. Once in the desired shape the dental wedge will undergo the "training" or "setting" steps to retain the final form of the wedge. The first and second sidewalls in the V-shape configuration can be deformed to be spaced apart by approximately 10-15 degrees.

A combination of heat-treating and cold working with control the final properties of the NiTi. Specifically, Austenite start temperature $A_S$ and finish temperature $A_F$ are preferably within a range encountered outside of the patient's mouth where the ambient temperature will be less than the temperature in the interproximal space between the first and second teeth. This enables the wedge to transform from its weaker, low temperature Martensite state to the stronger, higher temperature Austenite state while the dental professional is placing the dental wedge 10. The $A_S$-$A_F$ range must be formed while enabling the wedge to generate and apply a suitable expansion force on the tooth being restored and adjacent tooth to separate the teeth at least 30 microns and preferably between 50-100 microns and for the expansion force to be consistently applied over a timeframe of 5-10 minutes with the restoration is completed.

Likewise, the Martensite start temperature $M_S$ and finish temperature $M_F$ range must occur at the typical ambient room temperature less than the temperature present in the interproximal space between the first and second teeth or across a range of cooling temperatures readily attainable by refrigeration, freezing or exposure to a coolant spray. Preferably, the wedge shape cut from the NiTi sheet is cooled to below its $A_S$ temperature and then formed into its final configuration seen in FIG. 2. The shape of the dental wedge 10 is set into the NiTi by next heating the formed material to between 500-550° C. (932-1022° C.). The heat treatment time will determine the final $A_F$ temperature, preferably 30° C. (86° F.). At this $A_F$ temperature the dental wedge will return fully to its preferred shape while in the interproximal space between the tooth being restored and the adjacent tooth, but also provides the dental professional using the dental wedge enough time to set the wedge before its returns to its set shape. Rapid quenching of the heated dental wedge is required to set the NiTi into its desired memory shape. A single forming and "setting" cycle is contemplated for an embodiment of the present invention where the wings 42a, b, 44a, b are coplanar with the interior portions 40a, b of the first and second sidewalls 22, 24. Further aging of the NiTi once set into its desired shape may also be utilized to finalize the $A_F$ temperature. Due to the complex geometry of the dental wedge 10 it is contemplated that the wings 42a, b, 44a, b may be formed and "trained" into the NiTi sheet in a first step and then sidewalls 22, 24 and bridge 26 formed and "trained" into the NiTi sheet in a second step.

The dental wedge 10 may also be manufactured by a variety of conventional polymer processing techniques, including, for example, extrusion, injection molding, liquid injection molding, compression molding, reaction injection molding, pressing, drawing, and die cutting.

Figure 11:
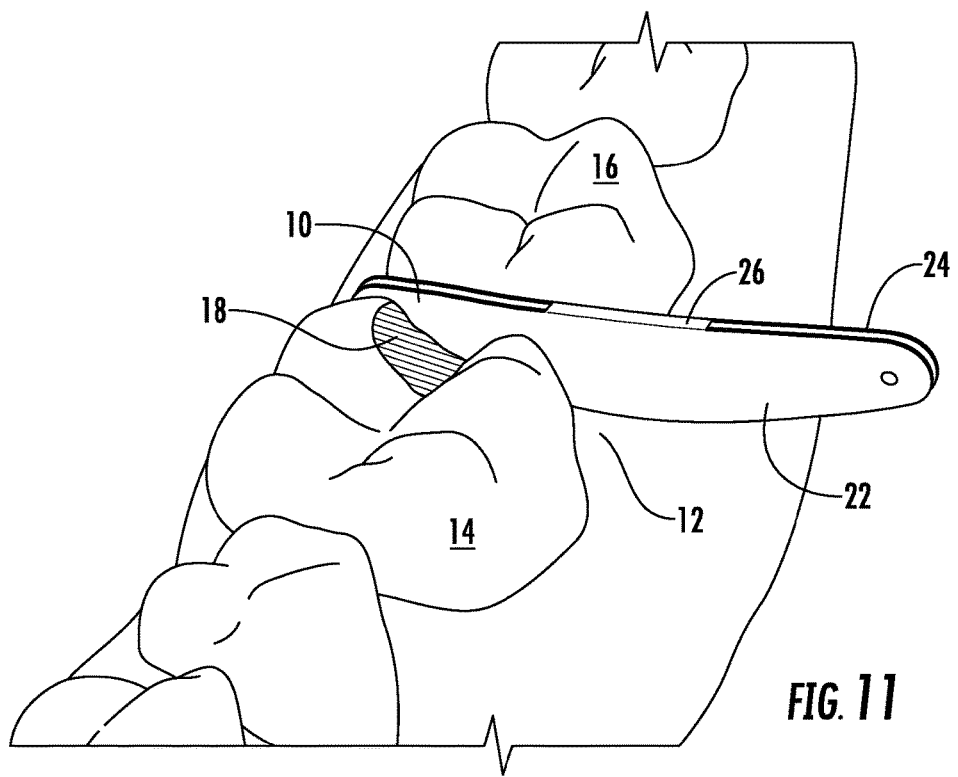

In operation after the dental carry or damaged portion 20 is removed and the restoration area 18 is prepared, the dental wedge 10 in its shape memory form (FIG. 3) will be cooled to below its $M_F$ temperature where it can be manipulated into a shape suitable for easy insertion into the interproximal space 12 between the tooth being restored 14 and adjacent tooth 16 (FIG. 11). When the dental wedge 10 includes through holes 48, a pin tweezers 50 may be utilized to grab and place the dental wedge 10 in the interproximal space 12 (FIG. 9). If the dental wedge 10 lacks through holes a standard dental instrument 56 with flat surfaces may be preferable to grab and place the dental wedge 10 into the interproximal space 12 (FIG. 10).

Figure 12:
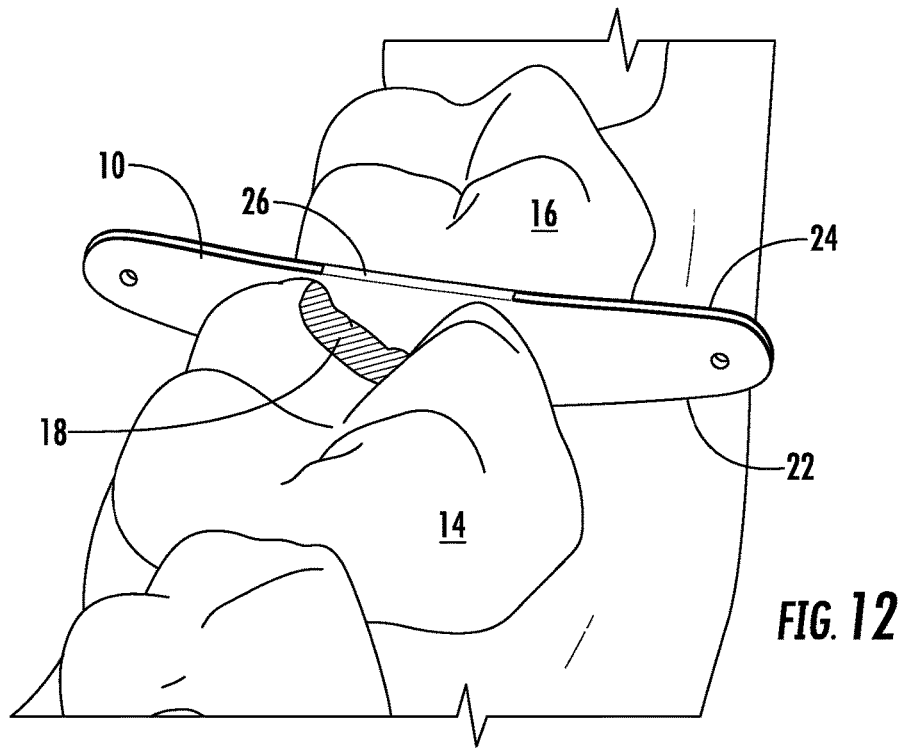
Figure 13:
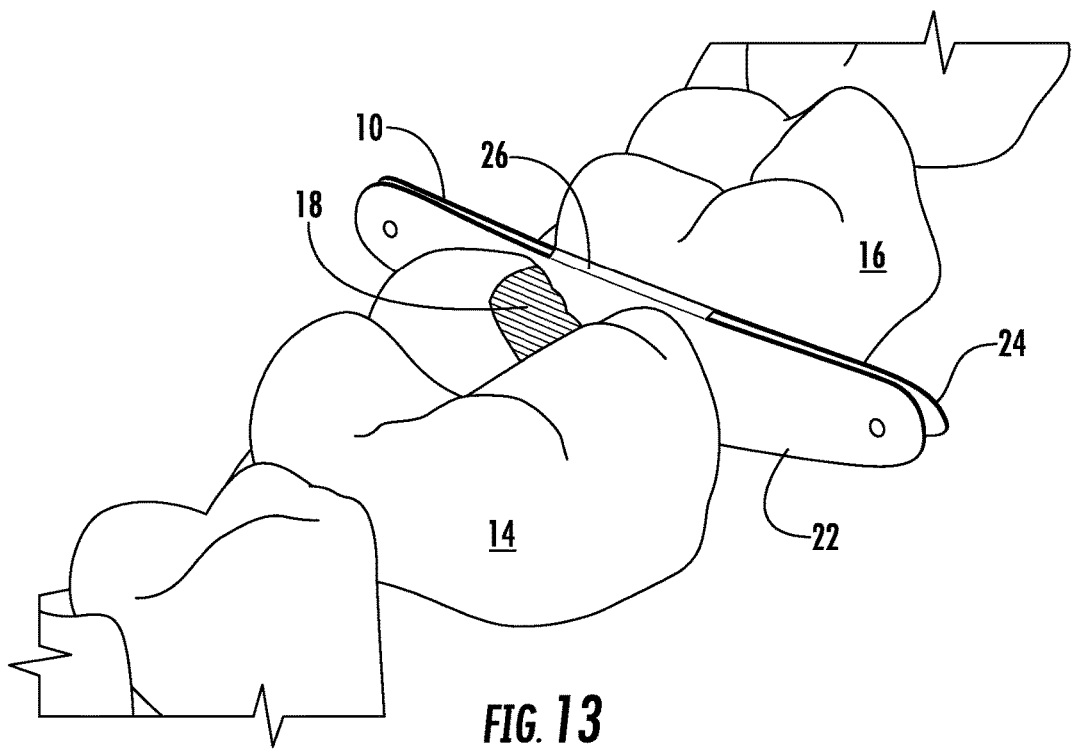
Figure 14:
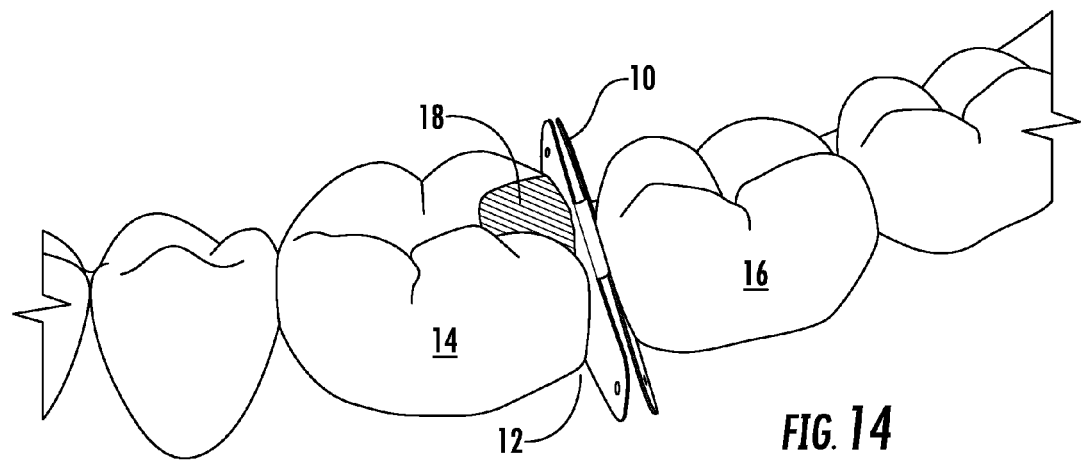
Figure 15:
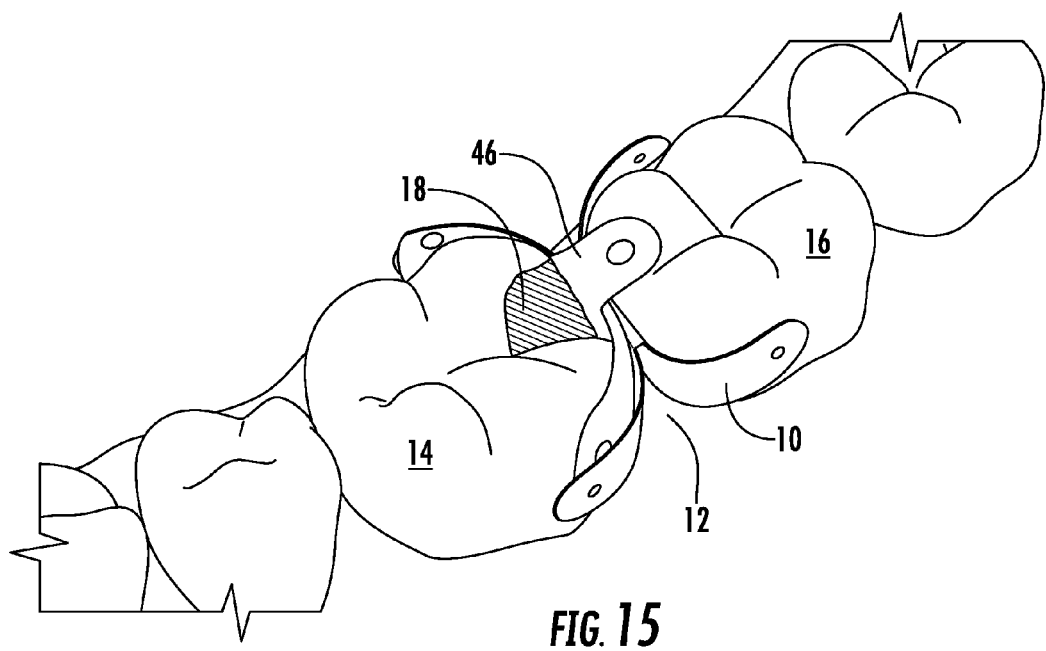

As seen in FIG. 12, the dental wedge 10 is properly placed when the bridge 26 is substantially or entirely located between the first and second teeth 14, 16. As the dental wedge returns to its pre-shaped form it will expand and exert an expansion force on the first and second tooth 14, 16. When the wings 42a, b, 44a, b of the first and second sidewalls 22,24 are set in a curved shape, the curvature will return to form as the dental wedge returns to its pre-shaped form (FIG. 1). If the pre-shaped form of the dental wedge does not include the curved wings, only the sidewalls 22, 24 will open (FIGS. 13-14). When the restoration procedure is complete the dental professional may remove the dental wedge from the interproximal space between the teeth by grasping it with a pin tweezers or other suitable dental instrument and pulling it from the interproximal space. While the dental wedge generates a sufficient expansion force the dental wedge will maintain a degree of flexibility. Depending the location and size of the restoration are 18 the first or second sidewall 22, 24 may be sufficient to assume the role of a dental matrix in containing the restoration material. Optionally, as seen in FIG. 15, a dental matrix 46 may be utilized and held into place against the tooth being restored 14 by the expansion force of the dental matrix 10.

While the present invention has been described in connection with a specific application, this application is exemplary in nature and is not intended to be limiting on the possible applications of this invention. It will be understood that modifications and variations may be effected without departing from the spirit and scope of the present invention. It will be appreciated that the present disclosure is intended as an exemplification of the invention and is not intended to limit the invention to the specific embodiments illustrated and described. The disclosure is intended to cover, by the appended claims, all such modifications as fall within the scope of the claims.

I claim:

1. A dental wedge to insert into the interproximal space between a first tooth being restored and a second, adjacent tooth, the dental wedge comprising:
   a first sidewall comprising an internal portion and configured to engage the first tooth;
   a second sidewall comprising an internal portion and configured to engage the second tooth;
   a bridge comprising a substantially planar member, said bridge being disposed between and connecting an upper edge of the first sidewall and an upper edge of the second sidewall to form an inverted V-shaped cross section throughout the internal portions of the first sidewall and second sidewall, wherein said upper edges of first and second sidewalls essentially lie in a plane of the top surfaces of said teeth;
   the first sidewall and second sidewall consisting essentially of a shape memory material enabling the first sidewall and second sidewall to transform from a first, resting state wherein the dental wedge is readily deformable to a second, operational state wherein the dental wedge returns to the inverted V-shaped cross section throughout the length of the internal portions of the first and second sidewalls and exerts an expansion force on the first tooth being restored and the second, adjacent tooth and
   wherein the first sidewall has a first length and the second sidewall has a second length and the bridge has a third length and wherein the third length is substantially less than the first length and the third length is also substantially less than the second length, and
   wherein the first length, the second length, and the third length are along a longitudinal axis of the wedge, wherein said longitudinal axis passes through the lingual and buccal sides of said teeth.

2. The dental wedge of claim 1 wherein the shape memory material comprises a shape memory alloy.

3. The dental wedge of claim 2 wherein the shape member alloy is a nickel-titanium alloy.

4. The dental wedge of claim 3 wherein the nickel-titanium alloy is in a Martensite phase when the dental wedge is in its first, resting state and wherein the nickel-titanium alloy is in an Austenite phase when the dental wedge is in the second, operational state.

5. The dental wedge of claim 4 wherein the transformation from the Martensite phase to the Austenite state occurs in response to the first transformation stimulus and the first transformation stimulus comprises a first ambient temperature less than a first interproximal space temperature present in the interproximal space between the first and the second tooth.

6. The dental wedge of claim 4 wherein the transformation from the Austenite state to the Martensite state occurs in response to a second transformation stimulus comprising a second ambient temperature less than a first interproximal space temperature present in the interproximal space between the first and the second tooth.

7. The dental wedge of claim 1 wherein the dental wedge is formed from a single piece of shape memory material and the first sidewall, second sidewall, and bridge are integrally formed.

8. The dental wedge of claim 1 wherein the expansion force is sufficient to separate the first tooth being restored and the second, adjacent tooth.

9. The dental wedge of claim 8 wherein the expansion force is sufficient to separate the first and second tooth by at least 30 microns and up to 100 microns.

10. The dental wedge of claim 8 wherein the expansion force is sufficient to separate the first and second tooth by 50-100 microns.

11. The dental wedge of claim 1 wherein the expansion force is sufficient to secure the dental matrix against the first tooth.

12. The dental wedge of claim 1 wherein the dental wedge in the second, operational stage exerts the expansion force at a consistent rate over a first time period of 5-10 minutes.

13. The dental wedge of claim 1 wherein the first and second sidewalls in the V-shape configuration are space apart approximately 30 degrees in the second, operational state.

14. The dental wedge of claim 1 wherein the first and second sidewalls in the V-shape configuration can be deformed to be spaced apart by approximately 10-15 degrees.

15. The dental wedge of claim 4 wherein the Austenite phase has a start temperature $A_S$ and a finish temperature $A_F$ and the $A_F$ temperature is less than a first interproximal space temperature present in the interproximal space between the first and the second tooth.

16. The dental wedge of claim 4 wherein the Martensite phase has a start temperature $M_S$ and a finish temperature $M_F$ and the $M_S$ temperature is less than a first interproximal space temperature present in the interproximal space between the first and the second tooth.

17. The dental wedge of claim 1 wherein the first and second sidewalls each further comprise a first and second wing extending from the interior portion of the first and second sidewalls, the first wings of each of the first and second sidewalls and the second wings of each of the first and second sidewalls curving away from each other when the dental wedge is in the second, operational state.

18. The dental wedge of claim 1 wherein the shape memory material comprises a shape memory polymer.

19. A dental wedge to insert into the interproximal space between a first tooth being restored and a second, adjacent tooth, the dental wedge comprising:
  a first sidewall comprising an internal portion with a length and a first and second wing extending from the internal portion, the first sidewall configured to engage the first tooth;
  a second sidewall comprising an internal portion with a length and a first and second wing extending from the internal portion, the second sidewall configured to engage the second tooth;
  a bridge comprising a substantially planar member, said bridge being disposed between and connecting an upper edge of the first sidewall and an upper edge of the second sidewall to form an inverted V-shaped cross section throughout the length of the internal portions of the first sidewall and second sidewall and the first wings of each of the first and second sidewalls and the second wings of each of the first and second sidewalls curve away from each other, wherein said upper edges of first and second sidewalls essentially lie in a plane of the top surfaces of said teeth;
  the first sidewall and second sidewall consisting essentially of a shape memory material enabling the first sidewall and second sidewall to transform from a first, resting state wherein the dental wedge is readily deformable to a second, operational state wherein the dental wedge returns to the inverted V-shaped cross section throughout the length of the internal portions of the first and second sidewalls and exerts an expansion force on the first tooth being restored and the second, adjacent tooth and
  wherein the first sidewall has a first length and the second sidewall has a second length and the bridge has a third length and wherein the third length is substantially less than the first length and the third length is also substantially less than the second length, and
  wherein the first length, the second length, and the third length are along a longitudinal axis of the wedge, wherein said longitudinal axis passes through the lingual and buccal sides of said teeth.

20. The dental wedge of claim 19 wherein the shape memory material comprises a shape memory alloy.

21. The dental wedge of claim 20 wherein the shape member alloy is a nickel-titanium alloy.

22. The dental wedge of claim 21 wherein the nickel-titanium alloy is in a Martensite phase when the dental wedge is in its first, resting state and wherein the nickel-titanium alloy is in an Austenite phase when the dental wedge is in the second, operational state wherein the Martensite phase has a start temperature $M_S$ and a finish temperature $M_F$ and the $M_S$ temperature is less than a first interproximal space temperature present in the interproximal space between the first and the second tooth and wherein the Austenite phase has a start temperature $A_S$ and a finish temperature $A_F$ and the $A_F$ temperature is less than a first interproximal space temperature present in the interproximal space between the first and the second tooth.

23. The dental wedge of claim 19 wherein the expansion force is sufficient to secure the dental matrix against the first tooth and is sufficient to separate the first tooth being restored and the second, adjacent tooth.

24. The dental wedge of claim 19 wherein the shape memory material comprises a shape memory polymer.

* * * * *